US011577335B2

(12) United States Patent
Huh (10) Patent No.: US 11,577,335 B2
(45) Date of Patent: Feb. 14, 2023

(54) DEVICE AND METHOD OF CONTROLLING WELDING HELMET

(71) Applicant: OTOS WING CO., LTD., Seoul (KR)

(72) Inventor: Moon Young Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 1259 days.

(21) Appl. No.: 16/004,807

(22) Filed: Jun. 11, 2018

(65) Prior Publication Data

US 2018/0290226 A1 Oct. 11, 2018

Related U.S. Application Data

(63) Continuation of application No. PCT/KR2017/014305, filed on Dec. 7, 2017.

(30) Foreign Application Priority Data

Dec. 7, 2016 (KR) .......................... 10-2016-0166131

(51) Int. Cl.
*B23K 9/095* (2006.01)
*B23K 9/32* (2006.01)
*A61F 9/06* (2006.01)

(52) U.S. Cl.
CPC ............ *B23K 9/0953* (2013.01); *A61F 9/061* (2013.01); *A61F 9/067* (2013.01); *B23K 9/0956* (2013.01); *B23K 9/322* (2013.01)

(58) Field of Classification Search
CPC .................. B23K 9/0953; B23K 9/322; B23K 9/095–0956; A61F 9/061; A61F 9/067;
(Continued)

(56) References Cited

U.S. PATENT DOCUMENTS 5,533,206 A 7/1996 Petrie et al.
6,070,264 A 6/2000 Hamilton et al.
(Continued)

FOREIGN PATENT DOCUMENTS

EP 2275061 1/2011
KR 101130222 3/2012
(Continued)

OTHER PUBLICATIONS

International Search Report—PCT/KR2017/014305 dated Apr. 13, 2018.

*Primary Examiner* — John J Norton
(74) *Attorney, Agent, or Firm* — Cantor Colburn LLP (57) ABSTRACT

Provided is a welding helmet control device comprising: a welding sensor or a light sensor configured to detect presence and intensity of welding light; a controller configured to count presence, intensity, and elapsed time of welding light, detected by the welding sensor or the light sensor, and to determine welding intensity, weld time, resting time, and weld number; a memory configured to store the welding intensity, the weld time, the resting time, and the weld number; a display configured to display the welding intensity, the weld time, the resting time, and the weld number, stored in the memory; a shutter driver configured to drive a shutter liquid crystal display (LCD) to vary a darkness concentration under control of the controller; and a setting unit configured to receive a setting value and a manipulation command, set by a user, and to transmit the received information to the controller.

5 Claims, 6 Drawing Sheets

(58) Field of Classification Search
CPC .... A61F 9/064; A61F 9/06–068; Y10T 29/49; Y10S 2/906
USPC .......... 219/130.01, 130.5; 319/14; 2/8.1–8.8
See application file for complete search history.

(56) References Cited

U.S. PATENT DOCUMENTS

| | | | |
|---|---|---|---|
| 2008/0158502 A1 | 7/2008 | Becker et al. | |
| 2011/0251838 A1* | 10/2011 | Huh | B23K 37/006 704/8 |
| 2013/0291271 A1* | 11/2013 | Becker | B23K 9/322 2/8.2 |
| 2013/0340141 A1* | 12/2013 | Huh | A61F 9/067 2/8.8 |
| 2015/0135389 A1* | 5/2015 | Yang | A61F 9/06 2/8.8 |
| 2016/0022496 A1* | 1/2016 | DeKeuster | G02F 1/13306 349/14 |
| 2017/0289424 A1* | 10/2017 | Beeson | B23K 25/00 |

FOREIGN PATENT DOCUMENTS

| | | |
|---|---|---|
| KR | 20150101444 | 9/2015 |
| KR | 101657141 | 9/2016 |

\* cited by examiner

DEVICE AND METHOD OF CONTROLLING WELDING HELMET

TECHNICAL FIELD

The present invention relates to a device and method of controlling a welding helmet, and more particularly to a device and method of controlling a welding helmet, for measuring welding operation time and cumulative time using a light sensor or a welding sensor, measuring a number of times spot welding (tack welding) is performed to measure spot welds per sec/min/hour, applying a stored welding condition to measure actual welding time, and easily converting a current mode into a grind mode during welding and, in particular, for conveniently storing a current welding condition, and easily moving a current state to a previous state of a welding condition and a set state via setting.

BACKGROUND ART

In general, arc welding refers to a process that is used to locally heat and dissolve metal using the fusibility of metal to join two metals and, in this regard, a worker puts on a welding helmet as one of protective devices for protection of the worker from heat, light, and gas which are generated during a welding process.

In the case of a welding helmet with a handle, it is cumbersome to release a welding helmet when in use and then to repeatedly and frequently hold and release a handle several times for every welding process.

The aforementioned welding helmet has been developed as a band type helmet and has been developed and studied to enhance work efficiency. In particular, a welding helmet is used to protect the eyes and face during an operation such as welding or cutting. In addition, the welding helmet includes an antiglare device (hereinafter, referred to as a cartridge) that is fixedly installed therein to protect user's eyes from intense harmful light generated during an operation such as welding or cutting.

In general, the cartridge blocks light with a wavelength equal to or greater than 780 nm (ib) and less than 365 nm (uv) and controls transmittance of visible light to allow a worker to perform a process while visually checking a welding position without glare.

U.S. Pat. No. 5,533,206 discloses a welding helmet including a liquid crystal display (LCD) lens that is directly positioned in front of eyes of a worker to actually function as a view window, a solar cell that absorbs light to function as an energy input unit, an electronic quick change (EQC) cartridge including an optical sensor cell that detects sparks and other intense light to function as a circuit input unit for automatically adjusting the LCD lens in a variable opacity state, and a cartridge housing positioned in a helmet to fixedly install the EQC cartridge in the helmet.

U.S. Pat. No. 6,070,264 discloses a shutter installed to allow a helmet wearer to see a welding process, an electronic controller coupled to the shutter to control light penetration shade of the shutter, an optical sensor for allowing the electronic controller to detect light emitted from the welding processing, and an electronic circuit for driving the shutter to be darker than before in response to the optical sensor that detects bright light from the welding process.

However, such a welding helmet includes a cartridge that detects intense light generated during a welding process to automatically drive an LCD lens and a shutter to be dark to protect the eyes of a worker against intense light but there is a problem in that it is difficult to measure spot welds per sec/min/hour and actual welding time and it is not possible to conveniently convert a current mode into a grind mode during welding.

It is not possible to rapidly convert a current condition into a desired welding condition in a grind mode during a welding operation and, thus, there is a problem in that it is too cumbersome to newly set a welding condition.

DISCLOSURE

Technical Problem

Therefore, the present invention has been made in view of the above problems, and it is an object of the present invention to provide a device and method of controlling a welding helmet, for measuring welding operation time and cumulative time using a light sensor or a welding sensor (cartridge LCD darkness sensor), measuring a number of times spot welding is performed to measure spot welds per sec/min/hour, applying a stored welding condition to measure actual welding time, and easily converting a current mode into a grind mode during welding or easily converting the grind mode into a welding mode.

It is another object of the present invention to provide a device and method of controlling a welding helmet, for converting a current mode into a grind mode during welding to perform welding and, then, rapidly converting a current mode into a previous mode or a mode set to a desired condition.

It is a further object of the present invention to provide a device and method of controlling a welding helmet, for converting a welding mode into a grind mode without taking off a helmet of a worker and for conveniently moving a current mode to a previous mode or a mode before the previous mode.

It is a further object of the present invention to provide a device and method of controlling a welding helmet, for setting one or more welding conditions to a cartridge controller and configured with a dial-type switch to store a current welding state and to find and use the state in next welding.

Technical Solution

In accordance with the present invention, the above and other objects can be accomplished by the provision of a welding helmet control device including a welding sensor or a light sensor configured to detect presence and intensity of welding light, a controller configured to count presence, intensity, and elapsed time of welding light, detected by the welding sensor or the light sensor, and to determine welding intensity, weld time, resting time, and weld number, a memory configured to store the welding intensity, the weld time, the resting time, and the weld number, determined by the controller, a display configured to display the welding intensity, the weld time, the resting time, and the weld number, stored in the memory, a shutter driver configured to drive a shutter liquid crystal display (LCD) to vary a darkness concentration under control of the controller, a setting unit configured to receive a setting value and a manipulation command, set by a user, and to transmit the received information to the controller, wherein the setting unit inputs a plurality of welding conditions and stores the input welding conditions in the memory, wherein the controller measures a number of times tack welding is performed to measure spot welds per minute and actual weld time, and wherein the welding helmet control device further includes a setting selection switch configured to set any one of pre-stored welding conditions and a grind mode conversion switch configured to convert a welding mode into a grind mode during a welding operation and to convert a current mode into a welding mode that is a previous mode when a grinding operation is terminated according to a predetermined condition.

Setting of the welding conditions may include shielded metal arc welding, $CO_2$ welding, tungsten inert gas (TIG)-welding, metal inert gas (MIG)-welding, and so on.

The setting unit may be formed on a cartridge and the setting selection switch and the grind mode conversion switch may be formed as a dial-type switch on a lateral surface of a welding helmet.

The controller may detect presence and intensity of welding light from the light sensor to check operation time of continuous welding, measure operation time of spot welding, which is equal to or greater than predetermined time, to increase cumulative number, measure operation time of continuous welding, which is equal to or greater than predetermined time after the cumulative number is increased, to increase cumulative time, and apply the cumulative time to measurement of the actual welding time.

In accordance with another aspect of the present invention, there is provided a method of controlling a welding helmet including inputting a plurality of welding conditions through a setting unit and storing the input information in a memory, measuring a number of times tack welding is performed to measure welds per sec/min/hour by a controller, setting any one of pre-stored welding conditions through a setting selection switch, measuring actual welding time by the controller, and converting a welding mode into a grind mode upon receiving information corresponding to a grind mode conversion switch during a welding operation and converting a current mode into a welding mode that is a previous mode when a grinding operation is terminated according to a predetermined condition.

The welding conditions may include a type and thickness of an iron plate as a welding target.

The setting unit may be formed on a cartridge and the setting selection switch and the grind mode conversion switch may be formed on a lateral surface of the welding helmet.

The measuring of the actual welding time by the controller may include detecting presence and intensity of welding light from the light sensor to check operation time of continuous welding, measuring operation time of spot welding, which is equal to or greater than predetermined time, to increase cumulative number, measuring operation time of continuous welding, which is equal to or greater than predetermined time after the cumulative number is increased, to increase cumulative time, and applying the cumulative time to measurement of the actual welding time.

Advantageous Effects

According to a device and method of controlling a welding helmet according to the present invention, welding operation time and cumulative time may be measured using a welding sensor or a light sensor, a number of times spot welding is performed may be measured to measure spot welds per sec/min/hour, a stored welding condition may be applied to measure actual welding time, and a current mode may be easily converted into a grind mode during welding or the grind mode may be easily converted into a welding mode.

Resting time may be measured and a time interval between welding operations may be measured to enhance operation efficiency, and an actual operation of a worker per minute and hour may be measured.

In addition, a welding mode may be converted into a grind mode without taking off a helmet of a worker, a separate conversion switch may be formed or a button or a dial-type switch may be formed to conveniently move a current mode to a previous mode or a mode before the previous mode, one or more welding conditions may be set to a cartridge controller, and a current welding state may be stored and may be found and used in subsequent welding.

In particular, a dial-type switch for grind mode conversion setting and a dial-type switch for mode setting selection may each be formed and, in addition, may be selectively formed to allow a worker to conveniently use the switch.

BEST MODE

As the invention allows for various changes and numerous embodiments, particular embodiments will be illustrated in the drawings and described in detail in the written description. In the description of the present invention, certain detailed explanations of the related art are omitted when it is deemed that they may unnecessarily obscure the essence of the invention.

Reference will now be made in detail to the exemplary embodiments of the present invention with reference to the accompanying drawings.

Figure 1:
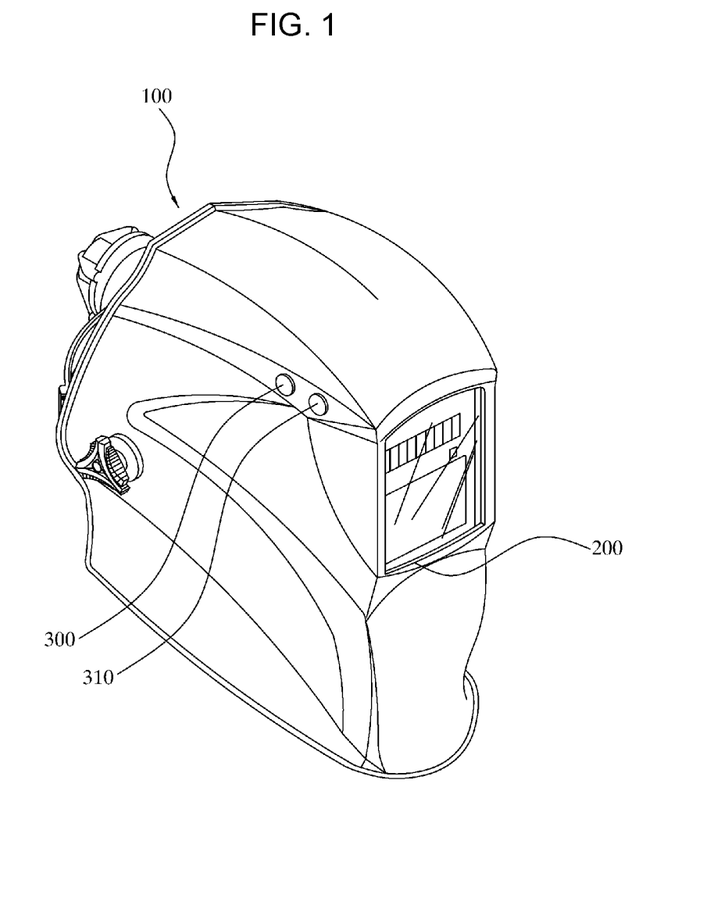
FIG. 1 is a perspective view showing an outer appearance of a welding helmet according to the present invention.
Figure 2:
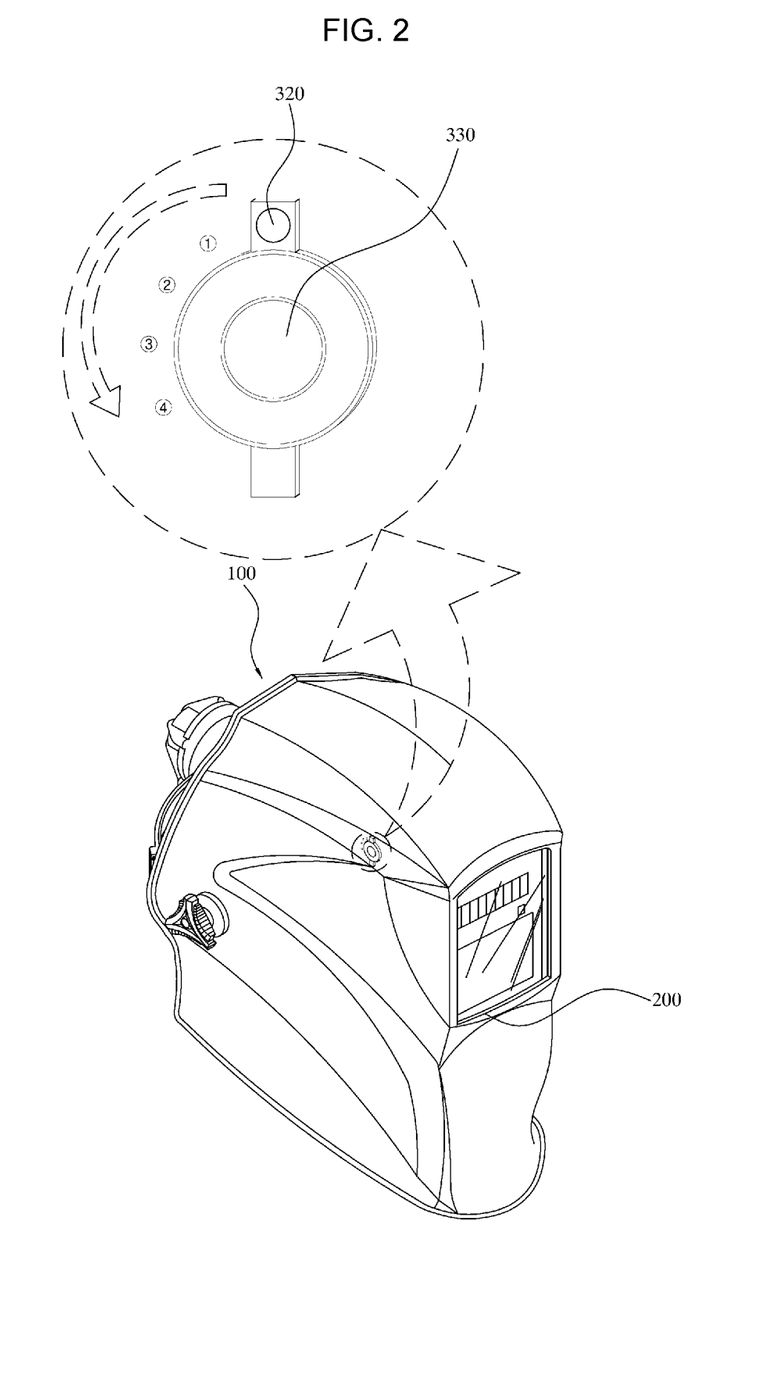
FIG. 2 is a perspective view of a switch to be of a dial type according to an embodiment of the present invention.
Figure 3:
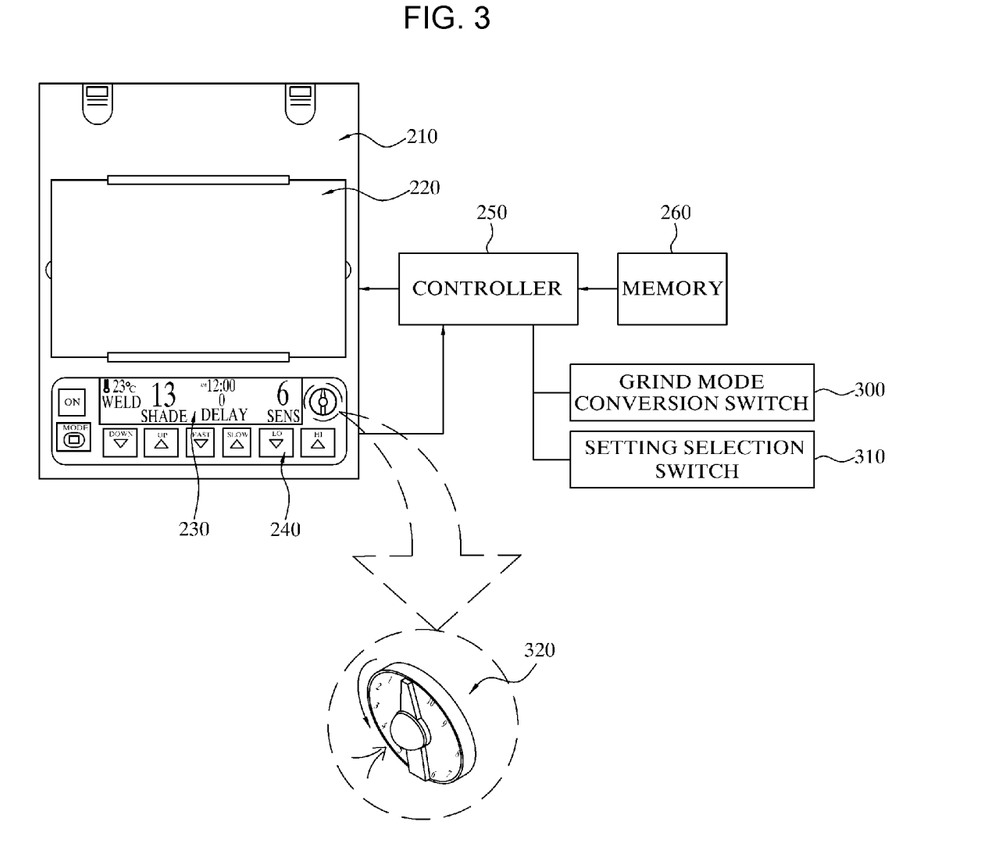
FIG. 3 is a detailed diagram showing a cartridge of the welding helmet according to the present invention.

FIG. 1 is a perspective view showing an outer appearance of a welding helmet according to the present invention and FIG. 2 is a perspective view of a switch to be of a dial type according to an embodiment of the present invention. In addition, FIG. 3 is a detailed diagram showing a cartridge of the welding helmet according to the present invention.

As illustrated, a welding helmet 100 according to the present invention may include a cartridge 200 and the cartridge 200 may include a main body 210, a shutter liquid crystal display (LCD) 220, a display 230, and a setting unit 240.

As illustrated in FIG. 1, a grind mode conversion switch 300 and a setting selection switch 310 may each be formed on the welding helmet 100.

As illustrated in FIG. 2, a button 330 for grind mode conversion and a dial-type operation unit 320 for mode setting selection may each be formed on the welding helmet 100.

The welding helmet 100 may be formed to protect and cover a face of a worker and may include the cartridge 200 installed on a front surface portion of the welding helmet 100.

The welding helmet 100 may be formed of a lightweight material such as an incombustible plastic.

The main body 210 of the cartridge 200 may configure an outer appearance of the cartridge 200 and may include a controller 250 including a general central processing unit (CPU) and a memory 260, which are installed in the main body 210.

Darkness concentration of the shutter LCD 220 may be set according to a user manipulation command or control of the controller 250 and the shutter LCD 220 may be driven with variable darkness concentration according to driving of a shutter driver 221.

A worker may wear the welding helmet 100, may cover his or her face with the cartridge 200 at the front surface portion and, then, may perform welding or cutting with appropriate brightness through an operation of the shutter LCD 220.

The display 230 may display a user input state, a device operation state, or the like.

The setting unit 240 may receive a setting value and a manipulation command set by a user and may transmit the received information to the controller 250. The setting unit may include the dial-type operation unit 320 that is formed thereon to store current welding states 1, 2, 3, 4, 5, 6, and 7 and includes a rotation part and a pushing part for searching for a previous welding state in a dial-type manner.

The controller 250 may control an overall operation state of a device and the memory 260 may store a data value based on a setting value and an operation state.

In particular, the setting unit 240 may input a plurality of welding conditions and may store the input information in the memory 260 and the controller 250 may measure a number of times tack welding is performed to measure spot welds per sec/min/hour and actual weld time.

The setting selection switch 310 may set any one of pre-stored welding conditions and the grind mode conversion switch 300 may convert a welding mode into a grind mode during a welding operation and may convert a current mode into a welding mode that is a previous mode when a grinding operation is terminated according to a predetermined condition.

Here, setting of one or more welding conditions may include setting 1, setting 2, setting 3, setting 4, setting 5, and setting 6 and, for example, setting 1 may be set to shielded metal arc welding, setting 2 may be set to $CO_2$ welding, setting 3 may be set to tungsten inert gas (TIG)-welding, setting 4 may be set to metal inert gas (MIG)-welding, any welding, and so on.

In addition, a welding state may be recognized through an optical sensor and a welding sensor (cartridge LCD darkness sensor) and information on a state of a welding condition may be stored to store information on operation time according to the welding condition.

A configuration and operation of the welding helmet configured as described above according to the present invention will be described in more detail.

Figure 4:
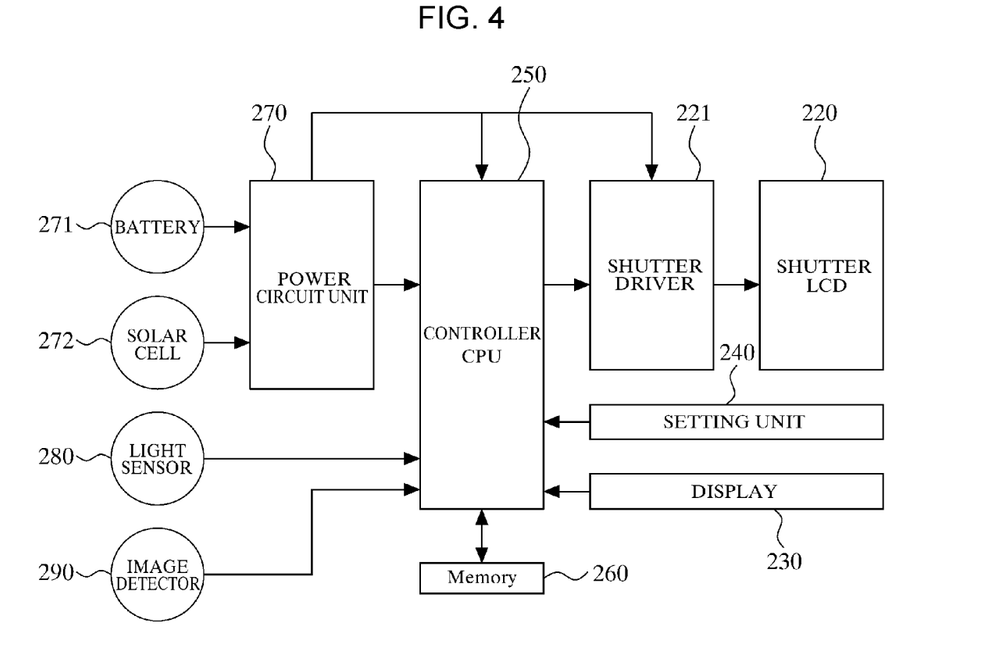
FIG. 4 is a block diagram showing a welding helmet control device according to the present invention.

FIG. 4 is a block diagram showing a welding helmet control device according to the present invention.

As illustrated, the welding helmet control device according to the present invention may include the shutter LCD 220, the shutter driver 221, the display 230, the setting unit 240, the controller 250, the memory 260, a power circuit unit 270, a battery 271, a solar cell 272, a light sensor 280, and an image detector 290.

The power circuit unit 270 may supply power collected from the battery 271 or the solar cell 272 to each unit.

A welding sensor or the light sensor 280 may detect presence and intensity of welding light.

The image detector 290 may detect an image of a welding state.

The controller 250 may count presence, intensity, and elapsed time of welding light, detected by the light sensor 280, and may determine welding intensity, weld time, resting time, and weld number.

The memory 260 may store the welding intensity, the weld time, the resting time, and the weld number, determined by the controller 250. The memory 260 may store the image of the welding state, detected by the image detector 290.

The display 230 may display the welding intensity, the weld time, the resting time, and the weld number, stored in the memory 260.

The shutter driver 221 may drive the shutter LCD 220 to vary a darkness concentration.

The setting unit 240 may receive the setting value and the manipulation command, set by the user, for example, a darkness concentration and an operating time of the shutter LCD 220 or may transmit information on a current welding condition or an existing welding condition to the controller 250.

In this case, a procedure of determining weld time by the controller 250 according to the present invention is now described. First, when the light sensor 280 detects first welding light, a welding operation may be recognized to be started. Then, an elapsed time may be counted up to a time point when welding light is not detected to determine the weld time.

A procedure of determining resting time (inter-welding time interval) according to the present invention is now described. First welding light may be recognized not to be detected from the light sensor 280 and, then, an elapsed time may be counted up to a time point when welding light is detected to determine the resting time.

It may be possible to separately measure and store information on first operation time of a worker and non-working time.

A procedure of determining weld number according to the present invention is now described. A number of times that welding light is detected from the light sensor 280 may be counted to determine the weld number.

In addition, the procedure of determining the weld number is now described. Intensity of welding light from the light sensor 280 may be detected and the weld time may be counted. The weld time may be compared with a predetermined reference value to determine welding intensity depending on how long weld time is maintained at specific intensity.

The welding state may be detected by the image detector 290, stored in the memory 260 and, then, displayed on the display 230 according to user selection.

The setting unit 240 may input a plurality of welding conditions and store the input information in the memory 260 and the controller 250 may measure a number of times tack welding is performed to measure spot welds per sec/min/hour and actual weld time.

In this case, the setting selection switch 310 may set any one of pre-stored welding conditions and the grind mode conversion switch 300 may convert a welding mode into a grind mode during a welding operation and may convert a current mode into a welding mode that is a previous mode when a grinding operation is terminated according to a predetermined condition.

According to the present invention, to store information on a welding condition corresponding to a current state in which an operation is performed, when a button or a dial-type switch is pushed for a long time to completely store the information (store the information via rotation), it may be possible to indicate storing of the information via a signal sound or a lamp and to store a welding condition required for another operation in real time.

Figure 5:
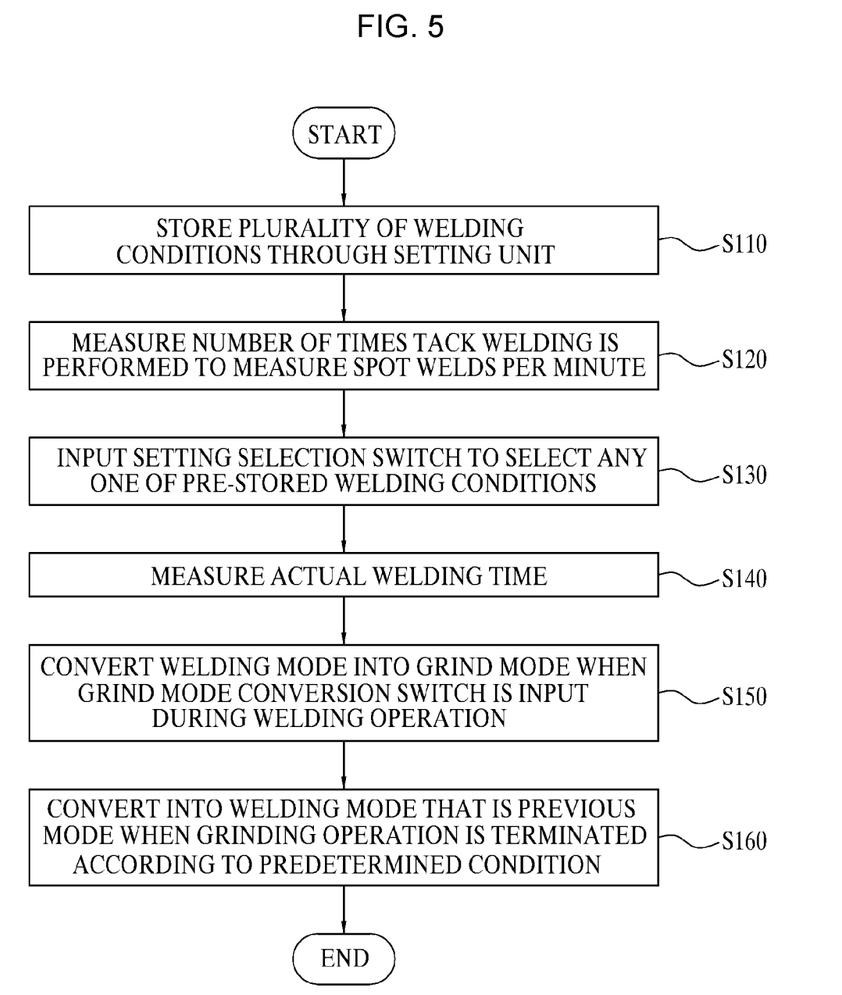
FIG. 5 is a control flowchart of a welding helmet control method according to the present invention.
Figure 6:
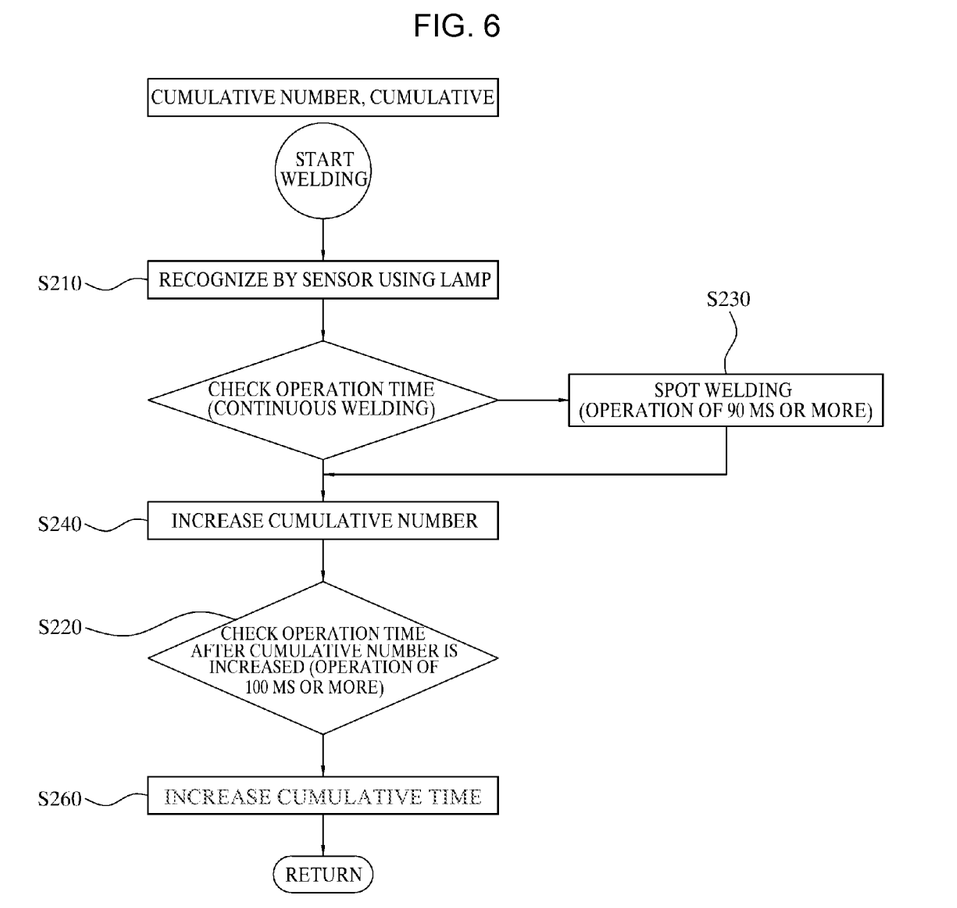
FIG. 6 is a detailed flowchart of a procedure of measuring cumulative number and cumulative time of FIG. 5.

FIG. 5 is a control flowchart of a welding helmet control method according to the present invention and FIG. is a detailed flowchart of a procedure of measuring cumulative number and cumulative time of FIG. 5.

As illustrated, the welding helmet control method according to the present invention may include inputting information on a plurality of welding conditions and storing the information in the memory 260 by the setting unit 240 (S110), measuring a number of times tack welding is performed to measure spot welds per minute by the controller 250 (S120), setting any one of pre-stored welding conditions by the setting selection switch 310 (S130), measuring actual weld time by the controller 250 (S140), upon receiving information corresponding to the grind mode conversion switch 300 during a welding operation, converting a welding mode into a grind mode, and converting a current mode into a welding mode that is a previous mode when a grinding operation is terminated according to a predetermined condition (S150 to S160).

Here, the welding condition may include a type and thickness of an iron plate as a welding target, any welding, and so on.

The setting unit 240 may be formed in the cartridge 200 and the setting selection switch 310 and the grind mode conversion switch 300 may be formed on one lateral surface of the welding helmet 100. A setting selection switch and a grind mode conversion switch may each be installed directly on the setting unit of the cartridge or may be installed separately therefrom.

As shown in FIG. 5, the measuring of the actual weld time by the controller 250 (S140) may include detecting presence and intensity of welding light to check operation time of continuous welding by the light sensor 280 and measuring operation time of spot welding, which is equal to or less than predetermined time (e.g., operation time of 100 ms or less), to increase a cumulative number (S210 to S240) and measuring operation time of continuous welding, which is equal to or greater than a predetermined time (e.g., operation time of 100 ms or more), to enhance cumulative time and to apply the cumulative time to the measuring of the actual welding time (S250 to S260).

Accordingly, according to the present invention, welding operation time and cumulative time may be measured using a light sensor, a number of times spot welding is performed may be measured to measure spot welds per sec/min/hour, a stored welding condition may be applied to measure actual welding time, and a current mode may be easily converted into a grind mode during welding or the grind mode may be easily converted into a welding mode.

Accordingly, the present invention may determine welding intensity, weld time, resting time, and weld number using a light sensor, may store the detected information in a memory, and may record, manage, and display a detailed welding state to more effectively perform welding.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A welding helmet comprising:
    a front surface portion;
    a lateral surface; and
    a welding helmet control device comprising:
        a welding sensor or a light sensor configured to detect the presence and intensity of welding light;
        a cartridge installed on the front surface portion of the welding helmet, the cartridge comprising
            a main body configuring an outer appearance of the cartridge and in which is installed
                a controller configured to count the presence, intensity, and elapsed time of welding light detected by the welding sensor or the light sensor, and to determine the welding intensity, weld time, resting time, and weld number; and
                a memory configured to store the welding intensity, the weld time, the resting time, and the weld number determined by the controller;
        a shutter liquid crystal display;
        a display configured to display the welding intensity, the weld time, the resting time, and the weld number stored in the memory; and
        a setting unit configured to receive a setting value and a manipulation command, set by a user, and to transmit the received information to the controller; and
        a shutter driver configured to drive the shutter liquid crystal display to vary a darkness concentration under control of the controller,
    wherein the setting unit is configured to input a plurality of welding conditions and store the input welding conditions in the memory;
    wherein the controller is configured to measure a number of times tack welding is performed to measure spot welds per minute and the weld time;
    wherein the welding helmet control device further comprises a setting selection switch configured to set any one of pre-stored welding conditions and a grind mode conversion switch configured to convert a welding mode into a grind mode during a welding operation and to convert a current mode into a welding mode that is a previous mode when a grinding operation is terminated according to a predetermined condition;
    wherein the setting selection switch and the grind mode conversion switch are formed as a dial-type switch on the lateral surface of the welding helmet and are formed on the cartridge as a dial-type operation unit configured to search for or input information on a current welding state; and
    wherein the controller is configured to detect the presence, the intensity, and the elapsed time of the welding light from the welding sensor or the light sensor to check the operation time of continuous welding, measure the operation time of tack welding to increase a cumulative number of the spot welds, measure the operation time of continuous welding after the cumulative number is increased to increase the cumulative weld time, and apply the cumulative weld time to the measurement of the welding time.

2. The welding helmet according to claim 1, wherein the welding conditions to be set comprises shielded metal arc welding, $CO_2$ welding, tungsten inert gas (TIG)-welding, and metal inert gas (MIG)-welding.

3. The welding helmet according to claim 1, wherein:
the welding helmet control device further comprises an image detector configured to detect an image of a welding state;
the memory is configured to store the welding state, detected by the image detector; and
the display is configured to display the welding state, stored in the memory.

4. A method of controlling the welding helmet according to claim 1, the method comprising:
inputting the plurality of welding conditions through the setting unit and storing the input information in the memory;
measuring the number of times tack welding is performed to measure the spot welds per minute by the controller;
setting any one of the pre-stored welding conditions through the setting selection switch;
measuring the welding time by the controller; and
converting the welding mode into the grind mode upon receiving information corresponding to the grind mode conversion switch during the welding operation, and converting a current mode into the welding mode that is a previous mode when the grinding operation is terminated according to a predetermined condition,
wherein the measuring of the welding time by the controller comprises detecting the presence and intensity of welding light from the light sensor to check the operation time of continuous welding, measuring operation the time of tack welding to increase a cumulative number of the spot welds, measuring the operation time of continuous welding after the cumulative number is increased to increase the cumulative weld time, and applying the cumulative weld time to the measurement of the welding time, and
wherein converting the welding mode into the grind mode comprises varying the darkness concentration of the shutter liquid crystal display, and converting the current mode into the welding mode comprises varying the darkness concentration of the shutter liquid crystal display.

5. The method according to claim 4, wherein the welding conditions comprises a type and thickness of an iron plate as a welding target.

* * * * *